United States Patent [19]

Hiramoto et al.

[11] 4,444,644

[45] Apr. 24, 1984

[54] PH ELECTRODE

[75] Inventors: Junichi Hiramoto; Shinichi Ohkawa, both of Osaka, Japan

[73] Assignee: Sumitomo Electric Industries, Ltd., Osaka, Japan

[21] Appl. No.: 348,885

[22] Filed: Feb. 16, 1982

[30] Foreign Application Priority Data

Feb. 17, 1981 [JP] Japan .................................. 56-21953

[51] Int. Cl.³ ...................... G01N 27/30; G01N 27/56
[52] U.S. Cl. .................................. 204/406; 204/433; 324/438; 357/25
[58] Field of Search .......... 357/25; 204/195 R, 195 B, 204/1 H, 433, 403, 406; 128/635; 324/438, 71.6

[56] References Cited

U.S. PATENT DOCUMENTS

| | | | |
|---|---|---|---|
| 3,642,600 | 2/1972 | Seiger et al. | 204/195 B |
| 4,020,830 | 5/1977 | Johnson et al. | 128/235 |
| 4,269,682 | 5/1981 | Yano et al. | 204/195 M |
| 4,305,802 | 12/1981 | Koshiishi | 204/195 M |

*Primary Examiner*—G. L. Kaplan
*Attorney, Agent, or Firm*—Sughrue, Mion, Zinn, Macpeak, and Seas

[57] ABSTRACT

A PH electrode is provided with an ISFET for generating a potential difference according to the PH value of an electrolyte to be measured, and includes a cell for driving the ISFET, so that the PH electrode can be used, as it is, with a conventional, potential difference type PH meter.

2 Claims, 5 Drawing Figures

PH ELECTRODE

BACKGROUND OF THE INVENTION

This invention relates to a PH electrode using an ISFET (ion-sensitive field-effect transistor) which can be used, without modification, with a conventional PH meter using a glass electrode.

FIG. 1 shows a conventional PH measuring circuit using a glass electrode. In FIG. 1, reference numeral 1 designates a PH meter (or a potentiometer); 2, electrolyte; 3, a reference electrode; and 4, a glass electrode. In order to electrically measure the PH value of the electrolyte, the PH meter using the glass electrode 4 has been extensively employed because its PH measurement range is wide and its measurement accuracy is high. The glass electrode 4 is in the form of a ball or a tube (whose diameter is 5 to 10 mm) made of a glass film in which a buffer solution whose PH value is known, and an electrode, are sealed. The potential difference between the glass electrode 4 and the reference electrode 3, which are inserted into the electrolyte 2, is in a certain relation to the PH value of the electrolyte 2. Therefore, the PH value of the electrolyte 2 can be determined by measuring the potential difference with the PH meter.

Shown in FIG. 2 is another conventional PH measuring circuit using an ISFET. In FIG. 2, reference numeral 5 designates the ISFET; and 6, a constant current source. Only recently have ISFETs been developed, and it has been known that the PH value of an electrolyte can be measured with an ISFET. When, under the condition that the ISFET is inserted into the electrolyte 2, a predetermined voltage $+V$ is applied to the source S of the ISFET and current is allowed to flow between the source S and the drain D thereof from the constant current source 6, the value of the voltage will depend on the PH value of the electrolyte 2. Therefore, the PH value of the electrolyte 2 can be measured by providing a voltage between the drain D and the reference electrode 3 as an output $V_{out}$. However, in order to measure the PH value with an ISFET, it has been necessary to provide the constant current source (6). Therefore, measurement could not be achieved using the PH measuring circuit with the conventional glass electrode.

SUMMARY OF THE INVENTION

Accordingly, an object of this invention is to provide a PH electrode using an ISFET which incorporates a cell, so as to be used in a conventional PH meter using a glass electrode.

The foregoing object and other objects of the invention have been achieved by the provision of a PH electrode using an ISFET for providing a potential difference according to the PH value of an electrolyte under measurement, which, according to the invention, comprises a cell as an operating DC source, so it may be used in a conventional potential difference type PH meter.

The nature, principle and utility of the invention will become more apparent from the following detailed description when read in conjunction with the accompanying drawings.

DETAILED DESCRIPTION OF THE PREFERRED EMBODIMENTS

Figure 1:
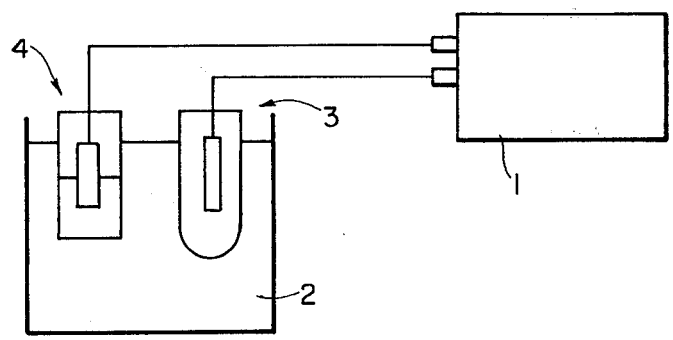
FIG. 1 is an explanatory diagram showing a conventional PH measuring circuit using a glass electrode.
Figure 2:
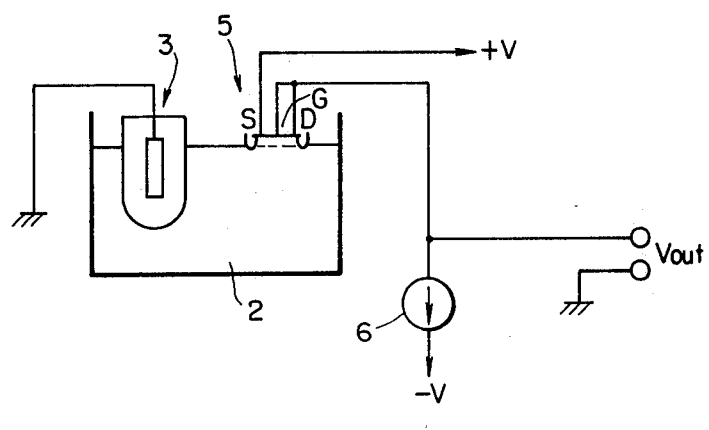
FIG. 2 is also an explanatory diagram showing another conventional PH measuring circuit using an ISFET.
Figure 3:
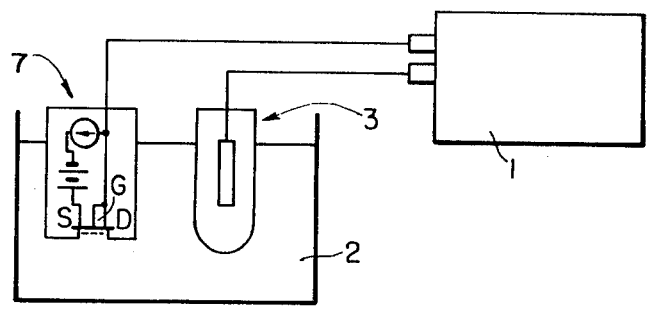
FIG. 3 is an explanatory diagram showing a PH measuring circuit which uses a PH electrode with an ISFET according to the invention.

FIG. 3 illustrates a PH measuring circuit with a PH electrode using an ISFET according to this invention. In FIG. 3, reference numeral 7 designates the PH electrode using the ISFET, which incorporates a cell. As is apparent from a comparison of FIGS. 1 and 3, the PH measuring circuit in FIG. 3 can be obtained by replacing the glass electrode 4 by the PH electrode 7. That is, the PH electrode 7 can be used in the conventional PH measuring circuit to replace the extensively used the glass electrode 4.

Figure 4:
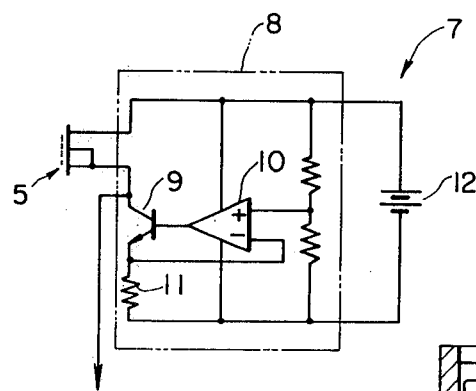
FIG. 4 is a circuit diagram of the PH electrode with the ISFET according to the invention.

FIG. 4 is a circuit diagram showing the PH electrode including the ISFET according to the invention. In FIG. 4, reference numeral 5 designates the ISFET; 8, a hybrid IC; and 12, the DC source. The hybrid IC 8 includes a transistor 9, an operational amplifier 10 and a resistor 11. The voltage developed according to the PH value of the electrolyte to be measured is provided at the collector of the transistor 9, and is detected through a connector.

Figure 5:
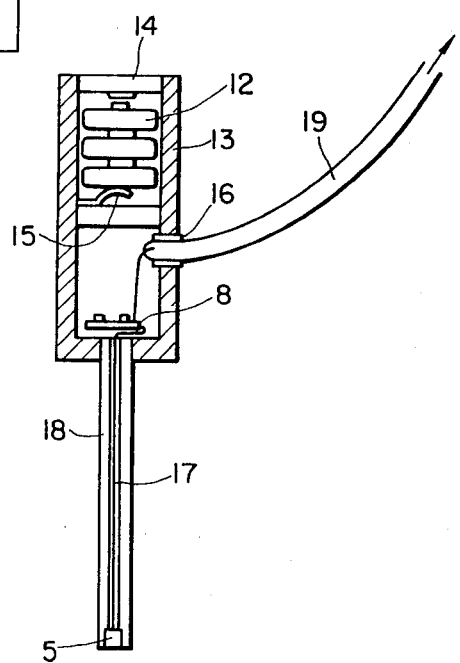
FIG. 5 is a front view, partly in section, showing the arrangement of one example of the PH electrode according to the invention.

FIG. 5 shows one example of the PH electrode using the ISFET according to the invention. In FIG. 5, reference numeral 5 designates the ISFET; 8, the hybrid IC; 12, the DC source cells; 13, a cell holder; 14, a cover which is threadedly engaged with the cell holder 13; 15, a retaining lever; 17, lead wires; 18, a glass tube; and 19, the cord. The hybrid IC 8 is built into the cell holder. The ISFET 5 is set at the end of the glass tube 18 which extends from the bottom of the cell holder 13. A part of the glass tube 18 is inserted into the electrolyte to be measured. The cord 19 is a single wire, and the connector may be the same as that connected to a commercially available PH electrode.

As may be seen from the foregoing, the aforementioned objects have been simply and efficiently attained. The ISFET PH detection of the invention incorporates the familiar cell containing tube structure including a glass tube, and is fully interchangeable with existing PH detection equipment.

What is claimed is:

1. A PH detecting apparatus, comprising; an electrode including an ion-sensitive field-effect transistor (ISFET) for providing a potential difference according to a PH value of an electrolyte solution under measurement, said electrode including an operating DC source connected to the source of said ISFET, said electrode further comprising, a circuit comprising an operational amplifier in parallel with said DC source, a resistor connected in series to one side of said DC source, said ISFET connected in series to the other side of said DC source, and a transistor having its emitter connected to said resistor, its base connected to said amplifier and its collector connected to said ISFET, an output being taken from the junction of a collector of said transistor and a drain of said ISFET, said electrode forming one input to a potential difference type PH apparatus, and a reference electrode forming a second input to said potential difference apparatus.

2. A device as claimed in claim 1, comprising said ISFET positioned at the end of a probe and a housing attached to said probe for said DC source, and said ISFET connected to said DC source and said collector of said transistor through lead wires.

* * * * *